United States Patent [19]
Gay et al.

[11] 3,965,183
[45] June 22, 1976

[54] PREPARATION OF p-FLUORO-m-PHENYLENEDIAMINE

[75] Inventors: Walter A. Gay, Cheshire; John H. Tobin, Beacon Falls, both of Conn.

[73] Assignee: Olin Corporation, New Haven, Conn.

[22] Filed: July 14, 1975

[21] Appl. No.: 595,613

[52] U.S. Cl. .............................. 260/578; 260/580; 260/582
[51] Int. Cl.² .................. C07C 85/11; C07C 85/12
[58] Field of Search ............... 260/578, 583 L, 582, 260/580

[56] References Cited
UNITED STATES PATENTS

| | | |
|---|---|---|
| 3,558,707 | 1/1971 | Churchill et al. .................. 260/580 |
| 3,574,034 | 8/1973 | Crocker .............................. 260/578 |
| 3,586,719 | 6/1971 | Bil et al. ............................. 260/578 |
| 3,832,364 | 8/1974 | Coulson ............................. 260/578 |
| 3,900,519 | 8/1975 | Gay et al. .......................... 260/580 |

*Primary Examiner*—Arthur P. Demers
*Attorney, Agent, or Firm*—Robert L. Andersen

[57] ABSTRACT p-Fluoro-m-phenylenediamine is prepared by deoxygenation and hydrofluorination of m-nitroacetanilide by the reaction of m-nitroacetanilide with anhydrous hydrogen fluoride at a temperature of 0°–230°C under a pressure of 15 to 1,500 psia in the presence of certain sulfur and phosphorus containing deoxygenating agents.

4 Claims, No Drawings

PREPARATION OF p-FLUORO-m-PHENYLENEDIAMINE

BACKGROUND OF THE INVENTION

The present invention relates to processes for preparing fluorinated m-phenylenediamines. More particularly the invention relates to the preparation of p-fluoro-m-phenylenediamine by reacting m-nitroacetanilide with HF and a selected deoxygenating agent at elevated temperature and pressure.

U.S. Pat. No. 3,588,707 discloses that reaction of nitrobenzene and substituted nitrobenzenes having at least one substituent selected from the group consisting of methyl, chloro, and nitro with anhydrous hydrogen fluoride and a deoxygenating agent produces a p-fluoroaniline. Where the starting nitrobenzene is dinitrobenzene the product is 3-nitro-4-fluoro-aniline. This product must be reduced still further to convert the second nitro group to an amine group and thus produce a corresponding fluoro-phenylenediamine.

One may speculate that the reduction of the second nitro group could be effected by doubling the amount of HF and deoxygenating agent in the initial reaction. This, however, would be wasteful and would likely produce a substantial amount of undesired difluorinated products. The alternative would be to conduct a second deoxygenation and fluorination which would have the same disadvantages.

The more logical approach would be to run a standard catalytic hydrogenation as a second step. Even if this reaction were carefully controlled some fluorine cleavage would probably occur. But more importantly, a second step would be required in a situation where it is desirable to go directly to the p-fluoro-m-phenylenediamine.

A second possible approach would be to dinitrate fluorobenzene and catalytically reduce the nitro groups. This however would require additional steps and the use of the more expensive fluorobenzenes as a starting material and is undesirable for both reasons.

We have found, however, that by simultaneously hydrofluorinating and deoxygenating m-nitroacetanilide, we can produce p-fluoro-m-phenylenediamine in a single reaction step. This is highly unexpected since it was previously thought that fluorinated products could not be formed from nitroacetanilides. Indeed, it has been found that it is only the m-nitroacetanilide which will undergo this reaction to produce fluorinated phenylenediamines, whereas ortho and para nitroacetanilides produce no fluorinated products.

SUMMARY OF THE INVENTION

In accordance with the present invention p-fluoro-m-phenylenediamine is therefore prepared by reacting together at elevated temperature and pressure m-nitroacetanilide, anhydrous hydrogen fluoride and a selected deoxygenating agent as hereinafter described.

DETAILED DESCRIPTION

The reaction according to the present invention proceeds according to the general equation:

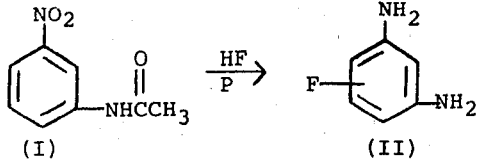

where P represents a suitable deoxygenating agent.

The reaction is conducted by heating m-nitroacetanilide (I) with anhydrous hydrogen fluoride at a temperature in the range of 0°–230°C under a pressure of from 15–1,500 psia in the presence of a deoxygenating agent selected from the group consisting of elemental phosphorus, elemental sulfur, phosphorus trihalides, sulfur halides in which sulfur has a valence less than 6, aryl phosphorus halides, aryl sulfenyl halides and triaryl phosphines.

Suitable starting materials include only m-nitroacetanilide in so far as is presently known, although it may be possible to utilize a m-nitroacetanilide which is substituted in the 2 or 5 positions with halogen, lower alkyl or lower alkyoxy substituents. The product (II) is primarily p-fluoro-m-phenylenediamine with the fluorine taking the position ortho to one amino group and para to the other with only a minor amount, if any, of substitution taking place at the carbon meta or ortho to both amino groups.

The starting material, m-nitroacetanilide, is available as such or may suitably be prepared by heating 3-nitroaniline with acetic anhydride or acetic acid as is well known to those skilled in the art.

Suitable deoxygenating agents include those disclosed in U.S. Pat. No. 3,558,707, namely red or yellow elemental phosphorus, elemental sulfur in any of its allotropic forms, phosphorus and sulfur halides including the fluorides, chlorides, bromides and iodides of trivalent phosphorous and of sulfur lower in valence than 6. Suitable examples include $PF_3$, $PCl_3$, $S_2Cl_2$, $SCl_2$, $SCl_4$, and $S_2Br_2$. Suitable aryl phosphorus and sulfur halides include, for example, diphenyl phosphorus chloride, di-p-tolyl phosphorus chloride and benzene sulphenyl chloride. Suitably triaryl phosphines include triphenyl phosphine, tri-o-tolyl phosphine, tri-p-tolyl phosphine and tri-p-bromophenylphosphine. Mixtures of these deoxygenating agents are also suitable.

In the process of this invention, the deoxygenating agents act as oxygen acceptors and form oxidation products, for example, $POCl_3$, $SOCl_2$ and triphenyl phosphine oxide. The by-products are easily separated from the product fluoro-m-phenylenediamines.

The anhydrous hydrogen fluoride supplies hydrogen for conversion of the nitro groups to $NH_2$ and supplies fluorine for substitution on the ring. It is important to maintain the hydrogen fluoride at least partly in the liquid phase and therefore the critical temperature of hydrogen fluoride at 230°C should not be exceeded. The pressures are suitably autogenous but higher pressures are also suitable if desired.

The various deoxygenating agents vary in activity and this affects the temperature at which the reaction may be conducted. For highly reactive deoxygenating agents such as benzene sulfenyl chloride atmospheric pressure and a temperature of °C is sufficient. It is preferred for most deoxygenating agents to utilize a temperature of 100°C –1200°C and more preferably 120°C –170°C.

The time required for the reaction also varies widely with different deoxygenating agents and satisfactory yields are obtained in from 1 to 10 hours or more, preferably 2–8 hours and most preferably 3 to 7 hours.

The amount of reactants employed is such that the molar rato of deoxygenating agent to m-nitroacetanilide is at least 0.3:1, preferably 0.5:1 up to 5:1. A molar ratio below 0.3:1 may be utilized but will cause yields to suffer. A molar ratio up to at least 10:1 may be utilized if desired but is generally not necessary. In the case of elemental phosphorus or sulfur it is intended that the molar ratio refers to the gram-atoms per mole of m-nitro-acetanilide.

The minimum stoichiometric molar ratio of hydrogen fluoride to m-nitro-acetanilide is 1:1. Less can be used, but the yields suffer. Preferably a molar ratio of hydrogen fluoride to m-nitro-acetanilide of at least 1:1 is used and molar ratios up to 50:1 are suitable but more hydrogen fluoride can be used, if desired. Preferably molar ratios of from 10:1 to 30:1 are used.

After the reaction is completed, the product is isolated in any convenient manner. For example, residual gasses are vented and HF is allowed to evaporate or is distilled off. Water is added to the residue, the residue then basified and the liberated amines extracted with a water immiscible organic solvent, such as diethyl ether, phased, and the solvent removed via vacuum stripping. The p-fluoro-m-phenylenediamine is then suitably separated from by-products of the reaction by distillation. The p-fluoro-m-phenylenediamine thus produced shares the utility of the fluorinated anilines, namely as an intermediate in the preparation of dyes, agricultural chemicals and pharmaceuticals as well as other chemicals.

It is thus a distinct advantage of the present invention that the basic reaction to form p-fluoro-m-phenylenediamine requires only a single reaction step. The precise mechanism of the reaction is not known and it is completely unclear why the meta isomer undergoes this reaction whereas the ortho and para isomers do not. It is also unclear at what stage of the reaction the hydrolysis of the amide to the amine occurs but it is of no significance in any event because the basification in the presence of water would be expected to hydrolyze any amide that remains unhydrolyzed at the end of the reaction.

Having thus fully described the invention the following example will demonstrate the preferred embodiment thereof.

EXAMPLE

A 300 ml Monel rocking autoclave was charged with 18.0 g (0.1 mol) m-nitroacetanilide, and 4.65 g (0.15 g atom) red phosphorus. The reactor was cooled to 30°C and 60g (3.0 mol) of anhydrous hydrogen fluoride added. The reactor was then sealed and heated while rocking to 150°C and 400 psig for 6 hours, then allowed to cool.

After the reactor had reached room temperature, the residual gases (10 psig) were vented and most of the hydrogen fluoride was allowed to evaporate. The residue was then diluted with 100 ml water and basified to pH 13 with 50% potassium hydroxide, extracted with diethyl ether, and phased. The ether portion was dried over magnesium sulfate, filtered and the solvent removed via vacuum stripping. Residual organic had a total weight of 11.3g and was analyzed via gas chromatography and mass spectroscopy. The following results were obtained at 100% conversion.

| Compound | Weight (g) | Yield |
|---|---|---|
| p-Fluoro-m-phenylenediamine | 3.19 | 25.3% |
| Fluoro-N-ethylphenylenediamine | 3.19 | 20.7 |
| m-Nitroaniline | 2.5 | 18.1 |
| N-Ethyl-3-nitroaniline | 1.1 | 6.5 |

What is claimed is:

1. A process for preparing p-fluoro-m-phenylene diamine comprising:
   reacting m-nitroacetanilide with anhydrous hydrogen fluoride in the presence a deoxygenating agent selected from the group consisting of elemental phosphorus, elemental sulfur, phosphorus trihalides, sulfur halides in which sulfur has a valence lower than 6, aryl phosphorus halides, aryl sulfenyl halides and triarylphosphines at a temperature in the range of 0°–230°C at a pressure in the range of 15 to about 1,500 psia.

2. The process of claim 1 wherein the molar ratio of hydrogen fluoride to m-nitroacetanilide is at least 1:1 and wherein the molar ratio of said deoxygenating agent to m-nitroacetanilide is at least 0.3:1.

3. The process of claim 2 wherein said deoxygenating agent is elemental phosphorus.

4. The process of claim 3 wherein said fluoro-m-phenylenediamine is recovered from the reaction mixture after basification.

* * * * *

PO-1050
(5/69)

UNITED STATES PATENT OFFICE
CERTIFICATE OF CORRECTION

Patent No. 3,965,183            Dated June 22, 1976

Inventor(s) Walter A. Gay and John H. Tobin

It is certified that error appears in the above-identified patent and that said Letters Patent are hereby corrected as shown below:

Column 2, line 58, "°C" should read --0°C--.

Column 2, line 60, "1200°C" should read --200°C--.

Column 2, line 67, the word "rato" should read --ratio--.

Signed and Sealed this

Eighth Day of February 1977

[SEAL]

Attest:

RUTH C. MASON
*Attesting Officer*

C. MARSHALL DANN
*Commissioner of Patents and Trademarks*